(12) United States Patent
Fukui

(10) Patent No.: US 8,287,897 B2
(45) Date of Patent: Oct. 16, 2012

(54) BITTERNESS-MASKING PARTICULATE JELLY BEVERAGE

(75) Inventor: Atsuko Fukui, Tokyo (JP)

(73) Assignee: Ryukakusan Co., Ltd., Tokyo (JP)

( * ) Notice: Subject to any disclaimer, the term of this patent is extended or adjusted under 35 U.S.C. 154(b) by 1445 days.

(21) Appl. No.: 10/571,504

(22) PCT Filed: Sep. 7, 2004

(86) PCT No.: PCT/JP2004/013279
§ 371 (c)(1),
(2), (4) Date: Mar. 5, 2007

(87) PCT Pub. No.: WO2005/025622
PCT Pub. Date: Mar. 24, 2005

(65) Prior Publication Data
US 2007/0231367 A1    Oct. 4, 2007

(30) Foreign Application Priority Data
Sep. 12, 2003  (JP) .................................. 2003-321623

(51) Int. Cl.
  *A61K 47/00* (2006.01)
  *A23L 1/05* (2006.01)
(52) U.S. Cl. .................... 424/439; 426/573; 426/590
(58) Field of Classification Search .................... None
See application file for complete search history.

(56) References Cited

U.S. PATENT DOCUMENTS

| 5,290,569 A * | 3/1994 | Nagafuzi et al. ............... 424/490 |
| 5,374,659 A * | 12/1994 | Gowan, Jr. .................... 514/557 |
| 5,932,235 A | 8/1999 | Ninomiya et al. |
| 6,180,159 B1 * | 1/2001 | Villagran et al. .............. 426/590 |
| 6,277,395 B1 | 8/2001 | Fukui et al. |
| 2003/0064107 A1 * | 4/2003 | Yu et al. ........................ 424/494 |
| 2005/0152975 A1 * | 7/2005 | Nakagami et al. ............ 424/469 |

FOREIGN PATENT DOCUMENTS

| JP | 05-255126 A | 10/1993 |
| JP | 09-194346 A | 7/1997 |
| JP | 11-124342 A | 5/1999 |
| JP | 2002-218917 A | 8/2002 |
| WO | WO 00/54811 A1 | 9/2000 |
| WO | WO 01/66083 A1 | 9/2001 |

OTHER PUBLICATIONS

Sugao et al. J Pharm Sci, 87(1), p. 96-100, 1998.*
Machine translation of WO 01/66083, original document published in 2001.*

* cited by examiner

*Primary Examiner* — Nissa Westerberg
(74) *Attorney, Agent, or Firm* — Knobbe, Martens, Olson & Bear, LLP

(57) ABSTRACT

A particulate jelly beverage which facilitates the intake of a bitter drug and/or supplement. The beverage comprises 0.1 to 15.0% bitterness-masking ingredient comprising a vegetable fat or animal fat, 5 to 20% bitterness-masking aid comprising a sugar alcohol, 0.1 to 5.0 % gellant such as an agar or carrageenan, and water as the remainder. It may optionally contain an ingredient for reducing water repellency, such as a sucrose/fatty acid ester, glycerol/fatty acid ester, or propylene glycol, in an amount of 0.01 to 1.5%.

10 Claims, No Drawings

BITTERNESS-MASKING PARTICULATE JELLY BEVERAGE

RELATED APPLICATIONS

This application is a U.S. National Phase filing under 35 U.S.C. §371 of International Patent Application No.: PCT/JP2004/013279, filed Sep. 7, 2004, which designated the United States, and which claims priority to Japanese Patent Application No. JP2003-321623, filed on Sep. 12, 2003, the content of each of which is hereby incorporated by reference in its entirety.

TECHNICAL FIELD

The invention relates to a granular jelly drink capable of masking bitter and, more particularly, to a granular jellylike beverage masking bitterness in various medicines and nutritional supplementary foods, i.e. dietary supplements, which include bitterness, and assisting and accelerating swallowing of medicine and the like to facilitate taking a medicine without difficulties or strange feeling for not only healthy persons but also patients, children and elderly persons who have difficulty in swallowing of medicine and the like using normal drinking water or the like for taking a medicine and the like due to various disease, frail constitution and so on.

BACKGROUND ART

Conventionally, it is general practice to take a medicine orally with water or plain hot water. However, it is difficult that patients, particularly elderly ones, who have difficulty in taking a medicine using such water or plain hot water. When a medicine in dosage form of powders, granules, capsules, tablets and the like is used internally, patients and the like do not swallow adequately, and then choke or remain such a medicine in the oral cavity, with the result that they not only do not gain enough curative effect but also sometimes feel discomfort.

Consequently, the way of grinding tablets, capsules and the like into meal or of mixing a medicine with food, such as boiled rice, miso soup, and juice, is employed to take a medicine. This is time-consuming and troublesome way. Furthermore, owing to grinding tablets, capsules, and the like into meal, a release time for medicinal components could not be controlled and a taste of such a medicine could not be masked, and then the desired effect of a medicine is sometimes not obtained.

In order to resolve these problems, the applicant proposed a swallowing assistive beverage with low calorie and sugar-free including a starch adhesive, such as agar and carrageenan, mannitol and the like and having the predetermined strength of jelly, which was granted a patent (c.f. see Patent Gazette No. 3257983).

The swallowing assistive beverage patented is applicable to take medicines in various dosage forms, does not hinder medicinal benefits, and does not inhibit the metabolism of insulin; accordingly the swallowing assistive beverage is well-suited to persons with dysphagia mentioned above, particularly those with chronic diseases, produces no side effects, and is usable with a sense of security for patients who supervene diabetes or the like.

However, the inventors, as the result of giving further consideration to the swallowing assistive beverage mentioned above, found room for further improvement therein.

The swallowing assistive beverage mentioned above, having also the function of wrapping a medicine, acts as an agent to mask a taste and a smell of ordinary medicines properly. On the other hand, the swallowing assistive beverage, due to having weak acid, sometimes accelerates the dissolution of a medicine in the oral cavity which includes bitterness, particularly powders, granules and the like including a basic material, such as an amino group, which has a nitrogen atom in chemical structure, and then it emerged that the swallowing assistive beverage does not have the enough effect of bitterness-masking yet.

DISCLOSURE OF THE INVENTION

The invention has been achieved in view of the inspection described above and the problems in such a conventional art. It is an object of the invention to provide a granular jelly drink capable of masking bitter which shows a superior bitterness-masking effect for a medicine and a dietary supplement including bitterness to facilitate taking them, improves swallowing of such a medicine and the like, has a simple construction, substitutes for normal drinking water, and does not inhibit medicinal benefits.

As a result of many keen examinations for achieving the object, the inventors found out that the object could be achieved by employing an animal and vegetable fat and oil as a bitterness-masking component, granular-jellifying in the solution state, and so on, and then have accomplished the invention.

In other words, the granular jelly drink capable of masking bitter of the invention is a granular jellylike beverage which facilitates taking a medicine and/or a dietary supplement including bitterness, comprising:

- 0.1 to 15.0% of a bitterness-masking component including a vegetable fat and oil and/or an animal fat and oil,
- 5 to 20% of a bitterness-masking supplemental component including a sugar alcohol,
- 0.1 to 5.0% of at least one of gelatinizing components selected from the group consisting of agar, carrageenan, gellan gum, furcellaran, gelatin, curdlan, psyllium seed gum, locust bean gum, xanthan gum, guar gum, pectin, arginic acid, arginic acid salt, mannan, and tamarind gum, and
- water as remains.

In preferred embodiment of the invention, the bitterness-masking granular jellylike beverage includes 0.01 to 1.5% of at least one of hydrofuge inhibition components selected from the group consisting of sucrose fatty acid ester, glycerine fatty acid ester, sorbitan fatty acid ester, propylene glycol, and propylene glycol fatty acid ester.

In another preferred embodiment of the invention, the bitterness-masking granular jellylike beverage has a pH of between 5 and 8.

In another preferred embodiment of the invention, the bitterness-masking granular jellylike beverage comprises a granular jelly with a jelly strength of 10 to 100 g/cm$^2$ at a temperature of 20 degrees C.

In another preferred embodiment of the invention, the bitterness-masking granular jellylike beverage comprises a granular jelly with a maximum length of 1 to 10 mm long.

In another preferred embodiment of the invention, the bitterness-masking granular jellylike beverage is effective in a medicine and/or a dietary supplement including bitterness as mentioned above whose dosage forms are one or more types of uncoated tablets, powders, fine granules, granules and syrups.

In another preferred embodiment of the invention, the bitterness-masking granular jellylike beverage is employed for an oral administration of a medicine which includes bitterness and comprises a basic material having within a molecule thereof a nitrogen atom derived from amino group and the like.

In another preferred embodiment of the invention, the bitterness-masking granular jellylike beverage is employed for an oral administration of a medicine which includes bitterness and is at least one selected from the group consisting of steroid, alkaloid, antibiotic, antibacterial agent, agents affecting the central nervous system, narcotic drugs, and Chinese herbal medicine. Particularly, it is more preferable that the antibiotic is either or both of macrolide antibiotic and cephem antibiotic.

In another preferred embodiment of the invention, the bitterness-masking granular jellylike beverage comprises a vegetable fat and oil of the aforementioned bitterness-masking components which is at least one selected from the group consisting of cacao fat and oil, lecithin, soybean oil, salad oil, edible safflower oil, sunflower seed oil, rapeseed oil, corn oil, rice oil, peanut oil, olive oil, sesame oil, linseed oil, coconut oil, palm oil, cocoanut oil, blended oil, margarine, and shortening: and an animal fat and oil thereof which is at least one selected from the group consisting of lard, salt-free butter, butter, cheese, cream, meat fat, and fish oil.

In another preferred embodiment of the invention, the bitterness-masking granular jellylike beverage comprises a sugar alcohol of the aforementioned bitterness-masking supplemental components which is at least one selected from group consisting of reduced maltose starch syrup, reduced starch syrup, reduced lactose, xylitol, erythritol, sorbitol, and mannitol.

Referring in detail to the granular jelly drink capable of masking bitter of the invention as follows. In this specification, "% (percent)" represents "mass percent", if not otherwise specified.

As described above, the bitterness-masking granular jellylike beverage of the invention includes a bitterness-masking component, a bitterness-masking supplemental component, a gelatinizing component, and water, and also includes a hydrofuge inhibition component as needed.

The bitterness-masking granular jellylike beverage does not belong to the category of a medicine and a dietary supplement, however, when used, is taken together with such a medicine and a dietary supplement.

The bitterness-masking component is at least one of types of a vegetable fat and oil and an animal fat and oil which binds rapidly to receptor in the taste buds of human to carry out the function of blocking out binding the bitterness component of a medicine and a dietary supplement with such a receptor of bitterness.

In fact, a human senses a taste from receptors called taste buds on and near the surface of the tongue. The taste bud measures a diameter of about 50 µm, and has taste cells internally. The receptors which sense acidity, saltiness, umami (i.e. the fifth taste sensation), and the like exist on the surface of the taste cell membranes. When the causative agent of bitterness included a medicine and the like binds bitterness sensing receptors, a taste cell is stimulated and creates a electric potential of difference and the electric potential of difference reaches a cerebral cortex through a nerve fiber, and then the bitterness is sensed.

In the invention, the bitterness-masking component mentioned above, through binding such a bitterness sensing receptor ahead of a bitterness component to cover the bitterness sensing receptor and blocking from binding the bitterness sensing receptor with the bitterness component, suppresses the stimulation of a taste cell and prevents from creating the electric potential of difference.

It is to be understood that the fat and oil of animals and vegetables mentioned above is not limited particularly in so far as the fat and oil carry out the function described above. Examples of vegetable fat and oil include cacao fat and oil, lecithin, soybean oil, salad oil, edible safflower oil, sunflower seed oil, rapeseed oil, corn oil, rice oil, peanut oil, olive oil, sesame oil, linseed oil, coconut oil, palm oil, cocoanut oil, blended oil, margarine, shortening, and a mixture of two or more of these. Examples of animal fat and oil include lard, salt-free butter, butter, cheese, cream, meat fat, fish oil, and a mixture two or more of these.

Preferred examples of the fat and oil of animals and vegetables include salt-free butter, butter, soybean oil, lecithin, olive oil, corn oil, and cacao fat and oil. Best example thereof is cacao fat and oil.

Examples of bitterness-masking components, except for a sort of the fat and oil of animals and vegetables mentioned above, may include milk, soy milk, and extracted component of these.

The bitterness-masking granular jellylike beverage of the invention includes an aforementioned bitterness-masking component of a blending quantity of 0.1 to 15.0%, preferably of 0.2 to 13.0%, more preferably of 0.25 to 11.0%.

The beverage which is blended the bitterness-masking component of less than 0.1% does not have enough effect in masking bitterness. The beverage which is blended the component of more than 15.0% causes a change of physical property of the jelly, with the result that the beverage which has an applicable strength of jelly is not provided.

A bitterness-masking supplemental component is one of sugar alcohols which act as a sweetening to have the assistive function of masking bitterness, and which also have the function of improving the stability of gel state.

Examples of the sugar alcohols include, but are not limited to particularly, reduced maltose starch syrup, reduced starch syrup, reduced lactose, xylitol, erythritol, sorbitol, mannitol, and a mixture of two or more of these. Preferred examples of such sugar alcohols include erythritol, reduced maltose starch syrup, reduced starch syrup, xylitol, and sorbitol.

The bitterness-masking granular jellylike beverage of the invention includes a bitterness-masking supplemental component of a blending quantity of 5 to 20%, preferably of 6 to 18.0%, more preferably of 8 to 16.0%. The beverage which is blended the bitterness-masking supplemental component of less than 5% does not have enough supplemental effect in masking bitterness. The beverage which is blended the bitterness-masking supplemental component of more than 20% reaches a level of saturation in bitterness-masking supplemental effect, and accordingly does not have significant difference with one which is blended the component of 20%.

It is all the requirement of the gelatinizing component only to be almost uniformly miscible with water in order to accelerate gelatinization.

Examples of gelatinizing components include agar, carrageenan, gellan gum, furcellaran, gelatin, curdlan, psyllium seed gum, locust bean gum, xanthan gum, guar gum, pectin, arginic acid, arginic acid salt, mannan, tamarind gum, and a mixture of two or more of these.

Preferred examples of such gelatinizing components include agar, carrageenan, xanthan gum, guar gum, and locust bean gum. Particularly, more preferred example thereof is locust bean gum.

The bitterness-masking granular jellylike beverage of the invention includes a gelatinizing component of a blending quantity of 0.1 to 5.0%, preferably of 0.1 to 4.0%, more preferably of 0.1 to 3.0%. The beverage which is blended the gelatinizing component of less than 0.1% does not have a jelly strength of greater than or equal to 10 g/cm². The beverage which is blended the component of more than 5.0% has an inapplicable physical property for taking a medicine and a dietary supplement.

The bitterness-masking granular jellylike beverage of the invention may include a hydrofuge inhibition component as needed.

The hydrofuge inhibition component has the function of inhibiting a hydrofuge quality of the bitterness-masking component mentioned above to improve the miscibility with water. In the case where the bitterness component mentioned hereinafter is slightly soluble in water, for example, lipid-soluble or in the case where a medicine has a waxy coating or a polymer coating in pharmaceutical formulation, the hydrofuge inhibition component increases the affinity between such bitterness component or such coating material and jelly, furthermore acts to enhance the function of wrapping effectively.

Examples of the hydrofuge inhibition component mentioned above include sucrose fatty acid ester, glycerine fatty acid ester, sorbitan fatty acid ester, propylene glycol, propylene glycol fatty acid ester, and a mixture of two or more of these.

The bitterness-masking granular jellylike beverage of the invention includes a hydrofuge inhibition component of a blending quantity of 0.01 to 1.5% preferably, more preferably of 0.02 to 1.4%, furthermore preferably 0.03 to 1.3%. The beverage which is blended the hydrofuge inhibition component of less than 0.01% does not have the enough effect of hydrofuge inhibition occasionally. The beverage which is blended the component of more than 1.5% reaches a level of saturation in the effect of inhibiting hydrofuge, and accordingly does sometimes not have significant differences with one which is blended the component of 1.5%.

In addition to the essential components described above, the bitterness-masking granular jellylike beverage of the invention, to in so far as exerting the effect of masking and assisting swallowing which fits for the purpose of the invention, may include a gelatinizing accelerator, a saccharide as a source of nutrient, a sweetening, a flavoring, and other additive agent.

For example, 0.01 to 2.0% of a sodium citrate may be added as a gelatinizing accelerator. 0.2 to 1.0% of a dextrin may be added as a gelatinizing supplemental accelerator.

It is all the requirement of the water which is included in the beverage of the invention only to be suitable for drink. Examples of the water include tap water, various types of ion-exchange water, and purified water.

Usually, the blending quantity of the water is determined like as the quantity of the water and each components described above amounts to 100% in all, that is, the quantity is the residual amount except for all the blended components.

Next, referring to the properties of the granular jelly drink capable of masking bitter of the invention.

The jellylike beverage is an aggregation substance of granular jelly, and typically has a pH of between 5 and 8, preferably of between 5.5 and 7.8, more preferably of between 5.7 and 7.6.

The beverage which has a pH of less than 5 has the possibility of eluting within the oral cavity a medical component which has a basic salt. The beverage which has a pH of more than 8 is at risk for infection with bacteria.

It is preferred that the jelly strength of granular jelly indicates 10 to 100 g/cm² at a temperature of 20 degrees C., more preferably 20 to 80 g/cm², furthermore preferably 20 to 70 g/cm².

The beverage which has a jelly strength of less than 10 g/cm² has the possibility of causing the disadvantage of making a person choke who has dysphagia and so on. The beverage which has a jelly strength of more than 100 g/cm² has the consistency like as inhibiting smooth swallowing occasionally.

A maximum length of a granular jelly, that is, a length of a longest imaginary line segment which runs the inside of a granular jelly in the shape of columnar, subulate, spheroidal, or the like generally, preferably measures 1 to 10 mm long, more preferably 1 to 8 mm long.

The beverage including a granular jelly which measures less than 1 mm in maximum length is in a state extremely near to paste and accordingly adheres and remains to a throat on rare occasion. The beverage including a granular jelly which measures more than 10 mm rarely exacerbates the adherability with a medicine and a dietary supplement.

The granular jellylike beverage of the invention, including such properties described above, has the appropriate strength of jelly and accordingly makes patients and children who have difficulty in swallowing due to frail constitution or various diseases and so on as well as healthy persons facilitate swallowing of various types of medicines and dietary supplements The granular jellylike beverage of the invention has the function of wrapping various types of medicines and accordingly makes persons who have the weakened contractive force of the muscles at the periphery of the throat and have the stricture of the esophagus due to the tension of the muscles feel the reduction of strange feeling for taking a medicine or a dietary supplement to swallow without choking. Concretely, the function of wrapping makes certain of wrapping even a readily water soluble powders to elute it little or nothing at room temperature and increases the number of pieces of solid medicines which is taken at one dose.

Further, the function of wrapping also accelerates to mask the bitterness and smell of a medicine and, specifically, inhibits effectively the release of a medicine and the like which is wrapped once in the oral cavity to elevate the function of masking bitterness. Therefore, the granular jellylike beverage of the invention is especially suitable for children or the like to take a medicine including intensely bitterness.

Furthermore, the bitterness-masking granular jellylike beverage of the invention, in spite of including the function of wrapping mentioned above, comprises water as most of the components to have no influence on the disintegration and dissolution of a medicine, and then occurs no interaction with a medicine not to hinder the medical effects of various medicines.

Besides, the granular jellylike beverage of the invention is sugar-free to suit even a diabetic, does not get a cavity easily even in the case of using just before bedtime to be also suitable for children, and is produced as a sterile beverage to use securely for children and patients who decline the physical strength, resistance, and immunity.

The granular jellylike beverage of the invention is a simple beverage comprising water and prescribed components as essentials and excels at the stability to facilitate taking the beverage anywhere if carrying a small bottle filling the beverage, and then it is a convenience for patients and the like to take a medicine and the like with the beverage when going out.

Next, referring to a method of preparation of a granular jelly drink capable of masking bitter of the invention as follows.

The granular jellylike beverage of the invention is produced by dissolving the gelatinizing component mentioned above in appropriate doses of water with warming, adding a bitterness-masking component, a bitterness-masking supplemental component, a hydrofuge inhibition component, and other additives in the solution, and dissolving all of them with warming and agitating.

The typical dissolution temperature, which can be changed as appropriate, stands at between 50 and 100 degrees C. in dissolving with warming. It is preferable that a resultant jelly, which is filled into container, is sterilized with retaining at a temperature of between 115 and 125 degrees C. during 10 to 30 minutes typically to prepare a germ-free beverage.

The bitterness-masking granular jellylike beverage resulted as described above allows taking together with various medicines and dietary supplements, specifically permits the way of, subsequent to putting a medicine or the like into the oral cavity, running the granular jellylike beverage replaced by water in the oral cavity and swallowing together with medicines and the like, and also the way of running the mixture of a medicine and the granular jellylike beverage prepared in advance into the oral cavity and swallowing them. Particularly, when the beverage is taken together with a medicine and/or a dietary supplement having bitterness, it is preferable to mix a medicine and the like with the beverage in a container, such as a glass, or to wrap a medicine and the like in the granular jellylike beverage before taking.

The bitterness-masking granular jellylike beverage of the invention is available for various medicines and dietary supplements, and particularly is preferable for the medicine which was previously treated as including bitterness and also as having difficulty in being swallowed.

The granular jellylike beverage of the invention is preferable for the medicines assumed to include especially strong bitterness among ones including bitterness. Examples of the medicines include clarithromycin, azithromycin, morphine and the like, that is, the medicine comprises a basic material having within a molecule thereof a nitrogen atom derived from amino group and the like.

Further, the granular jellylike beverage of the invention is preferable for the substances including strong bitterness among steroid drug, alkaloid, antibiotic, antibacterial agent, agents affecting the central nervous system, narcotic drugs, Chinese herbal medicine. Particularly, it is more preferred for macrolide antibiotic and cephem antibiotic.

While rare of taking two or more of such medicines together, the bitterness-masking granular jellylike beverage is preferable for taking the mixture of such medicines from the standpoint of masking bitterness and assisting in swallowing.

From the standpoint of dosage forms, powders, fine granules, granules, and syrups, particularly dry syrups, get caught in the gap between artificial teeth, adhere to mucous membrane in the mouth, and enter into the trachea not only to sense the bitterness but also to be liable to difficulty in swallowing. The granular jellylike beverage of the invention wraps such powders not only to prevent the adhesion thereof in the oral cavity but also to aggregate such powders. This brings the preferable effects of masking bitterness and assisting swallowing for such powders.

After swallowing a medicine with the beverage of the invention, the beverage of the invention is, different from taking a medicine with a cooling beverage as before, scarcely left in the oral cavity and leaves a lightly aftertaste. For such reasons, the beverage of the invention is especially suitable for persons who have artificial teeth.

The granular jellylike beverage of the invention, whose function of wrapping mentioned above is similar to a wafer, when warmed to body temperature, namely about a temperature of 37 degrees C., reduces the jelly strength thereof to lose the function of wrapping, and accordingly does not inhibit the disintegration and dissolution of a medicine in the body.

From the standpoint of assisting in swallowing, the granular jellylike beverage of the invention, which includes the appropriate jelly strength and the like mentioned above, wraps even tablets larger than 10 mm in diameter and capsules larger than size #1 to swallow them easily.

Conventionally, it is well known that the administration of a solid medicine and a powder medicine together has difficulty in swallowing. However, the granular jellylike beverage of the invention facilitates even such an administration, that is, to take two or more types of medicines having various dosage forms at a time.

BEST MODE FOR CARRYING OUT THE INVENTION

Hereinafter, the invention will be described in more detail by examples and comparative examples; however, the invention is not to be considered limited to what is shown in the examples.

EXAMPLE 1

Xylitol, reduced maltose starch syrup, and xanthan gum were dissolved in warmed water. While the solution was kept at a temperature of about 50 degrees C., salt-free butter, flavoring, and sweetening were added and dissolved in the solution, and then the solution was cooled down. Thus, the bitterness-masking granular jelly of the example was prepared. The composition is shown in table 1.

The strength of jelly indicated 14.5 g/cm$^2$, the granular jelly measured about 4.5 mm in maximum length, indicated a pH of 6.8 and a syneresis rate of 0.3%.

TABLE 1

| | Example 1 |
|---|---|
| xylitol | 5 |
| reduced maltose starch syrup | 10 |
| xanthan gum | 0.2 |
| salt-free butter | 2.5 |
| flavoring | 0.15 |
| stevia | 0.04 |
| purified water | 82.11 |
| total amount | 100 |

EXAMPLE 2

Erythritol, sorbitol, and tamarind gum were dissolved in warmed water. While the solution was kept at a temperature of about 50 degrees C., salt-free butter and flavoring were added, and then the solution was cooled down. Thus, the bitterness-masking granular jelly of the example was prepared. The composition is shown in table 2.

The strength of jelly indicated 22.2 g/cm$^2$, the granular jelly measured about 4.8 mm in maximum length, indicated a pH of 6.8 and a syneresis rate of 2.0%.

TABLE 2

| | Example 2 |
|---|---|
| erythritol | 10 |
| sorbitol | 10 |
| tamarind gum | 0.2 |

TABLE 2-continued

|  | Example 2 |
| --- | --- |
| salt-free butter | 2.5 |
| flavoring | 0.15 |
| purified water | 77.15 |
| total amount | 100 |

EXAMPLE 3

Erythritol, reduced maltose starch syrup, locust bean gum, xanthan gum, and agar were dissolved in boiling water. While the solution was kept at a temperature of about 50 degrees C., homogenized glycerine monofatty acid ester and soybean oil were added, subsequently flavoring and sweetening were added and dissolved, and then the solution was cooled down. Thus, the bitterness-masking granular jelly of the example was prepared. The composition is shown in table 3.

The strength of jelly indicated 49.8 g/cm$^2$, the granular jelly measured about 5.0 mm in maximum length, indicated a pH of 7.5 and a syneresis rate of 1.2%.

TABLE 3

|  | Example 3 |
| --- | --- |
| erythritol | 10 |
| reduced maltose starch syrup | 9 |
| locust bean gum | 0.1 |
| xanthan gum | 0.05 |
| Agar | 0.1 |
| soybean oil | 5 |
| flavoring | 0.15 |
| sucralose | 0.05 |
| glycerine monofatty acid ester | 0.4 |
| purified water | 75.15 |
| total amount | 100 |

EXAMPLE 4

Erythritol, reduced maltose starch syrup, locust bean gum, xanthan gum, carrageenan, and calcium lactate were dissolved in warmed water. While the solution was kept at a temperature of 50 degrees C., homogenized sucrose fatty acid ester and cacao fat and oil were added, and flavoring and sweetening were further added and dissolved, and then the solution was cooled down. Thus, the bitterness-masking granular jelly of the example was prepared. The composition is shown in table 4.

The strength of jelly indicated 39.8 g/cm$^2$, the granular jelly measured about 5.0 mm in maximum length, indicated a pH of 6.6 and a syneresis rate of 1.8%.

TABLE 4

|  | Example 4 |
| --- | --- |
| erythritol | 10 |
| reduced maltose starch syrup | 4 |
| locust bean gum | 0.1 |
| xanthan gum | 0.05 |
| carrageenan | 0.2 |
| calcium lactate | 0.1 |
| Cacao fat and oil | 0.8 |
| flavoring | 0.2 |
| stevia | 0.05 |

TABLE 4-continued

|  | Example 4 |
| --- | --- |
| sucrose fatty acid ester | 0.02 |
| purified water | 84.48 |
| total amount | 100 |

COMPARATIVE EXAMPLES 1 TO 3

Deionized water was used as a beverage of the comparative example 1, black tea which was extracted to steep one tea bag in hot water at a temperature of 75 degrees C. during 3 (three) minutes was used as a beverage of the comparative example 2, commercial sports drink which indicates a pH of 3.4 was used as a beverage of the comparative example 3.

COMPARATIVE EXAMPLE 4

Erythritol, locust bean gum, xanthan gum, agar, carrageenan, and pectin were dissolved in boiling water. Subsequently, citric acid, sodium citrate, and flavoring were added and dissolved in the solution, and then the solution was cooled down. Thus, the jellylike beverage of the comparative example was prepared. The composition is shown in table 5.

The strength of jelly indicated 46.6 g/cm$^2$, the granular jelly measured about 5.2 mm in maximum length, indicated a pH of 3.3 and a syneresis rate of 1.3%.

TABLE 5

|  | Example 5 |
| --- | --- |
| erythritol | 8.82 |
| locust bean gum | 0.05 |
| xanthan gum | 0.01 |
| Agar | 0.2 |
| carrageenan | 0.02 |
| pectin | 0.04 |
| Citric acid | 0.21 |
| sodium citrate | 0.14 |
| flavoring | 0.1 |
| purified water | 90.41 |
| total amount | 100 |

[Performance Evaluation]

The beverage of each example was subjected to the following human sensory examination and the results are shown in table 6.

(Condition of the Sensory Examination)

As described below, each of the samples was prepared by treating a specified amount of an intended medicine with the beverage of each example, and each of the resultant samples, which was a beverage containing medicine, was taken by 6 (six) of test subjects who are healthy adults. The capability of masking in the beverage of each example has been determined by means of the "bitterness" at the prescribed point in time. In table 6, the mark of "A", "B", "C", "D", and "E" represents "excellent", "good", "average", "unsuitable for use", and "very poor quality" respectively.

Intended Medicines (i) Clarith® (made in Taisho Pharmaceutical Co., Ltd., clarithromycin), dry syrup for children's use (ii) zithromac® (made in Pfizer Products Inc. azithromycin), fine granules for children's use Amount of the Medicine 0.5 g of each of the medicines was used. The prescribed pediatric dose of the intended medicine measures 1 g per 10 kg of body weight. It was assumed that the medicine was administered for a two years old child in 5 kg of body weight who was used most frequently.

Preparation of a Sample

Each sample is prepared by mixing 0.5 g of the intended medicine with 25 ml of the beverage of each example. The comparative examples 1 to 3 are stirred using a stirrer at room temperature, 200 rpm during more than 1 hour. The intended medicine is put on each of the jellylike beverages of the example 4 and the comparative example 4 and is mixed with a little quantity of the periphery of the jellylike beverage to wrap around the medicine.

Determination Points of Bitterness

The determination points of bitterness were following three; (a) five seconds later from putting a sample into the mouth, (b) just after the time when spitting out a sample and rinsing out the mouth with water five times, (c) five minutes later when finishing rinsing out the mouth.

TABLE 6

|  | (a) | (b) | (c) |
|---|---|---|---|
| Example 4 | (i) A | (i) A | (i) A |
|  | (ii) B | (ii) A | (ii) A |
| Comparative example 1 | (i) B | (i) B | (i) A |
|  | (ii) D | (ii) B | (ii) B |
| Comparative example 2 | (i) B | (i) A | (i) A |
|  | (ii) C | (ii) B | (ii) A |
| Comparative example 3 | (i) E | (i) D | (i) C |
|  | (ii) D | (ii) C | (ii) A |
| Comparative example 4 | (i) E | (i) D | (i) C |
|  | (ii) D | (ii) B | (ii) A |

The bitter taste strength of the beverage of each sample was measured with the use of the taste sensor device mentioned below. The measurement result of the bitter taste strength is shown in table 7. (Condition of the bitter taste strength measurement with the use of a taste sensor device)

Taste Sensor Device

Taste recognizer (trade name "SA402": made in Intelligent Sensor Technology Company)

The recognizer is a measuring device which is provided with an electrode part having a lipid membrane sensor, a robot arm, and an information analysis part, i.e. CPU. On the basis of the measured value of an electric potential of difference between a lipid membrane and a reference electrode, the bitter taste strength is calculated. The strength is indicated by indexes between 1 (one) and 6 (six), the bigger number of which expresses a stronger bitter taste strength.

Intended Medicine

Clarith (see the entry under human sensory examination)

Amount of the Medicine

Same as the human sensory examination mentioned above

Preparation of Samples

Same as the human sensory examination mentioned above

Determination Points of Bitterness

The following two points were selected:

(A) 5 (five) seconds later when a lipid membrane sensor and a reference electrode in a taste recognizer "SA402" is immersed in a measuring cell with an infill of each sample.

(B) At the point in time when a measuring cell which has been ejected a sample is rinsed with ion-exchanged water five times and is filled with ion-exchanged water.

TABLE 7

|  | (A) | (B) |
|---|---|---|
| Example 4 | 1.07 | 0.99 |
| Comparative example 1 | 1.30 | 1.10 |
| Comparative example 2 | 2.54 | 2.04 |
| Comparative example 3 | 5.08 | 2.94 |
| Comparative example 4 | 4.68 | 2.75 |

INDUSTRIAL APPLICABILITY

As referred above, the invention, as a result of being employed an animal and vegetable fat and oil as a bitter taste masking component, being granulated and jellified, and so forth, achieves to provide a granular jelly drink capable of masking bitter which shows a superior bitterness-masking effect for a medicine and a dietary supplement having bitterness to facilitate taking them, improves swallowing such a medicine and the like, has a simple composition, is substituted for normal drinking water, and also does not inhibit medicinal benefits.

For example, the bitterness-masking granular jellylike beverage of the invention achieves a superior bitterness-masking effect even for powders and granules which have strong bitterness and have extreme difficulty in drug processing. Particularly, the bitterness-masking granular jellylike beverage solves the problem that most of infants and children who take such a medicine frequently have serious troubles in a treatment such as refusing taking a medicine and vomiting after taking a medicine, and then conduces to prevent a fall of compliance in taking a medicine effectively.

The beverage of the invention relieves the pain of taking a medicine for a person who has to take a medicine and the like having strong bitterness for a prolonged period to suffer from chronic disease.

The granular jellylike beverage of the invention is superior in a swallowing assistance effect. To take a medicine and the like orally with the beverage enables a person who does not have enough faculties of swallowing, particularly infant and elderly person, to swallow easily without a stress from strange feeling and bitterness of a medicine and the like.

In this way, the granular jellylike beverage of the invention improves the QOL (Quality Of Life) of a person who feels a pain in taking a medicine and the like, and is contributory to live a comfortable life for them.

What is claimed:

1. A jelly drink capable of masking bitter for facilitating taking a medicine and/or a dietary supplement including bitterness, said drink comprising aggregated jelly granules, wherein the jelly drink comprises: 0.1 to 15.0% of a bitterness- masking component including at least one of a vegetable fat, vegetable oil, animal fat, and animal oil, 5 to 20% of a bitterness-masking supplemental component including sugar alcohol, 0.1 to 5.0% of at least one of gelatinizing components selected from the group consisting of agar, carrageenan, gellan gum, furcellaran, gelatin, curdlan, psyllium seed gum, locust bean gum, xanthan gum, guar gum, pectin, arginic acid, arginic acid salt, mannan, and tamarind gum, and water as remains;

wherein the maximum length of an individual jelly granule measures 1 to 10 mm; and wherein said jelly drink is packaged without said medicine and/or dietary supplement such that said drink is adapted to be mixed by an end user with said medicine and/or dietary supplement.

2. The jelly drink according to claim 1, wherein the drink further comprises 0.01 to 1.5% of at least one of hydrofuge inhibition components selected from the group consisting of sucrose fatty acid ester, glycerine fatty acid ester, sorbitan fatty acid ester, propylene glycol, and propylene glycol fatty acid ester.

3. The jelly drink according to claim 1, wherein the drink has a pH of 5 to 8.

4. The jelly drink according to claim 1, wherein the jelly strength of said drink indicates 10 to 100 g/cm² at 20 degrees C.

5. The jelly drink according to claim 1, which is used to take a medicine and/or a dietary supplement including bitterness wherein the medicine and/or the dietary supplement including bitterness is in a dosage form selected from one of uncoated tablets, powders, fine granules, granules, and syrups or the combination of two or more of these.

6. The jelly drink according to claim 1, which is used to take a medicine including bitterness, wherein the medicine includes a basic material having a nitrogen atom within a molecule.

7. The jelly drink according to claim 1, which is used to take a medicine including bitterness, wherein the medicine is at least one of medicines selected from the group consisting of steroid, alkaloid, antibiotic, antibacterial agent, agents affecting the central nervous system, narcotic drugs, and Chinese herbal medicine.

8. The jelly drink according to claim 7, wherein the antibiotic is macrolide antibiotic and/or cephem antibiotic.

9. The jelly drink according to claim 1,
wherein the vegetable fat and/or oil of the bitterness-masking component is at least one selected from group consisting of cacao fat, cacao oil, lecithin, soybean oil, salad oil, edible safflower oil, sunflower seed oil, rapeseed oil, corn oil, rice oil, peanut oil, olive oil, sesame oil, linseed oil, coconut oil, palm oil, cocoanut oil, blended oil, margarine, and shortening; and
wherein the animal fat and/or oil thereof is at least one selected from the group consisting of lard, salt-free butter, butter, cheese, cream, meat fat, and fish oil.

10. The jelly drink according to claim 1, wherein the sugar alcohol of the bitterness-masking supplemental component is at least one selected from the group consisting of reduced maltose starch syrup, reduced starch syrup, reduced lactose, xylitol, erythritol, sorbitol, and mannitol.

* * * * *

UNITED STATES PATENT AND TRADEMARK OFFICE
CERTIFICATE OF CORRECTION

| | |
|---|---|
| PATENT NO. | : 8,287,897 B2 |
| APPLICATION NO. | : 10/571504 |
| DATED | : October 16, 2012 |
| INVENTOR(S) | : Atsuko Fukui |

It is certified that error appears in the above-identified patent and that said Letters Patent is hereby corrected as shown below:

In the Specification

In Column 6, Line 23-24, please change "supplements" to --supplements.--.

In the Claims

In Column 12, Line 56-57, in Claim 1, please change "bitterness- masking" to --bitterness-masking--.

Signed and Sealed this
Twenty-third Day of December, 2014

Michelle K. Lee
*Deputy Director of the United States Patent and Trademark Office*